US011236328B2

(12) United States Patent
Ignoni et al.

(10) Patent No.: US 11,236,328 B2
(45) Date of Patent: *Feb. 1, 2022

(54) EUGLOBULIN-BASED METHOD FOR DETERMINING THE BIOLOGICAL ACTIVITY OF DEFIBROTIDE

(71) Applicant: GENTIUM S.R.L., Villa Guardia (IT)

(72) Inventors: Terenzio Ignoni, Solbiate (IT); Vijay Kumar, Casnate (IT); Khalid Islam, Massagno (IT)

(73) Assignee: GENTIUM S.R.L., Villa Guardia (IT)

( * ) Notice: Subject to any disclaimer, the term of this patent is extended or adjusted under 35 U.S.C. 154(b) by 0 days.

This patent is subject to a terminal disclaimer.

(21) Appl. No.: 17/459,169

(22) Filed: Aug. 27, 2021

(65) Prior Publication Data

US 2021/0388350 A1  Dec. 16, 2021

Related U.S. Application Data

(63) Continuation of application No. 17/396,028, filed on Aug. 6, 2021, which is a continuation of application No. 16/816,741, filed on Mar. 12, 2020, now Pat. No. 11,085,043, which is a continuation of application No. 15/844,801, filed on Dec. 18, 2017, now abandoned, which is a continuation of application No. 14/408,272, filed as application No. PCT/IT2012/000193 on Jun. 22, 2012, now Pat. No. 9,902,952.

(51) Int. Cl.
| | |
|---|---|
| *C12N 15/11* | (2006.01) |
| *C12N 9/68* | (2006.01) |
| *A61K 31/711* | (2006.01) |
| *A61K 38/36* | (2006.01) |
| *C12Q 1/37* | (2006.01) |
| *C12Q 1/56* | (2006.01) |
| *G01N 33/86* | (2006.01) |

(52) U.S. Cl.
CPC ............ *C12N 15/11* (2013.01); *A61K 31/711* (2013.01); *C12Q 1/37* (2013.01); *C12Q 1/56* (2013.01); *G01N 33/86* (2013.01); *C12N 2310/127* (2013.01)

(58) Field of Classification Search
None
See application file for complete search history.

(56) References Cited

U.S. PATENT DOCUMENTS

| | | |
|---|---|---|
| 3,770,720 A | 11/1973 | Butti et al. |
| 3,829,567 A | 8/1974 | Butti et al. |
| 3,899,481 A | 8/1975 | Butti et al. |
| 4,234,682 A | 11/1980 | Bartl et al. |
| 4,649,134 A | 3/1987 | Bonomini |
| 4,693,995 A | 9/1987 | Prino et al. |
| 4,694,134 A | 9/1987 | Ross |
| 4,753,221 A | 6/1988 | Kensey et al. |
| 4,853,221 A | 8/1989 | Elslager |
| 4,985,552 A | 1/1991 | Fedeli et al. |
| 5,081,109 A | 1/1992 | Ulutin |
| 5,116,617 A | 5/1992 | Mantovani et al. |
| 5,223,609 A | 6/1993 | Fedeli et al. |
| 5,231,006 A | 7/1993 | Kolde |
| 5,624,912 A | 4/1997 | Burcoglu et al. |
| 5,646,127 A | 7/1997 | Lanzarotti et al. |
| 5,646,268 A | 7/1997 | Lanzarotti et al. |
| 5,856,444 A | 1/1999 | Kawakita et al. |
| 5,919,772 A | 7/1999 | Szyf et al. |
| 5,977,083 A | 11/1999 | Burcoglu |
| 6,046,172 A | 4/2000 | Ennio et al. |
| 6,573,372 B2 | 6/2003 | McCall et al. |
| 6,699,985 B2 | 3/2004 | Burcoglu |
| 7,338,777 B2 | 3/2008 | Porta et al. |
| 7,785,797 B2 | 8/2010 | Wohlgemuth et al. |
| 8,551,967 B2 | 10/2013 | Ferro et al. |
| 8,980,862 B2 | 3/2015 | Iacobelli |
| 9,539,277 B2 | 1/2017 | Iacobelli |
| 9,867,843 B2 | 1/2018 | Iacobelli |
| 9,902,952 B2 | 2/2018 | Ignoni et al. |
| 10,393,731 B2 | 8/2019 | Ignoni et al. |
| 11,085,043 B2 | 8/2021 | Ignoni et al. |
| 2002/0142029 A1 | 10/2002 | Porta et al. |

(Continued)

FOREIGN PATENT DOCUMENTS

| | | |
|---|---|---|
| DE | 19740384 A1 | 3/1999 |
| EP | 0558833 A2 | 9/1993 |

(Continued)

OTHER PUBLICATIONS

"Defibrotide"—Clinic Medication, First Edition, Mar. 2000, pp. 887-888 with English translation.
"Defibrotide—Substance Summary," SIDS 51091757, PubChem Substance, Retrieved from http://pubchem.ncbi.nlm.nih.gov on Mar. 11, 2009, 3 pages.
"Everything you ever wanted to know concerning Oligonucleotides but were afraid to ask," downloaded Jul. 9, 2010 from http://www.auburn.edu/.about.santosr/protocols/OligoProtocols.pdf, 5 pages.
"Fibrinolytic System," Pediatric Hemorrhagic Diseases, First Edition, May 2009, Chapter 5, pp. 81-85 with English translation.

(Continued)

*Primary Examiner* — Marsha Tsay
(74) *Attorney, Agent, or Firm* — Cooley LLP

(57) ABSTRACT

It is disclosed a method for determining the biological activity of defibrotide, which comprises the steps of: a) bringing into contact defibrotide, mammalian euglobulin and a substrate specific for the plasmin which, by reaction with the plasmin, provides a measurable product; and b) measuring the amount of product formed at successive times, to thereby determine the biological activity of the defibrotide. Liquid defibrotide formulations are also disclosed, preferably water solutions, having a defined biological activity and, in particular, having an activity of 25 to 35 IU/mg of defibrotide, preferably from 27 to 32 IU/mg and, more preferably, from 28 to 32 IU/mg.

19 Claims, 2 Drawing Sheets

(56) References Cited

U.S. PATENT DOCUMENTS

| | | | |
|---|---|---|---|
| 2002/0155432 | A1 | 10/2002 | Schwartz et al. |
| 2003/0013669 | A1 | 1/2003 | Burcoglu |
| 2004/0131588 | A1 | 7/2004 | Ferro et al. |
| 2004/0248834 | A1 | 12/2004 | Klinman et al. |
| 2005/0009131 | A1 | 1/2005 | Porta et al. |
| 2005/0059629 | A1 | 3/2005 | Gaarde et al. |
| 2005/0196382 | A1 | 9/2005 | Vaillant et al. |
| 2005/0215498 | A1 | 9/2005 | Eissner et al. |
| 2007/0037144 | A1 | 2/2007 | Wohlgemuth et al. |
| 2009/0131362 | A1 | 5/2009 | Echart et al. |
| 2010/0254938 | A1 | 10/2010 | Ferro et al. |
| 2011/0092576 | A1 | 4/2011 | Stein et al. |
| 2012/0121698 | A1 | 5/2012 | Mehar et al. |
| 2013/0231470 | A1 | 9/2013 | Iacobelli |
| 2015/0176003 | A1 | 6/2015 | Ignoni et al. |
| 2015/0196580 | A1 | 7/2015 | Echart |
| 2015/0297624 | A1 | 10/2015 | Iacobelli |
| 2017/0080012 | A1 | 3/2017 | Iacobelli |
| 2017/0304349 | A1 | 10/2017 | Iacobelli |
| 2017/0322199 | A1 | 11/2017 | Ignoni et al. |
| 2018/0334672 | A1 | 11/2018 | Ignoni et al. |
| 2020/0057051 | A1 | 2/2020 | Ignoni et al. |

FOREIGN PATENT DOCUMENTS

| | | | |
|---|---|---|---|
| EP | | 0937461 A1 | 8/1998 |
| EP | | 1059092 A1 | 12/2000 |
| EP | | 1147777 A1 | 10/2001 |
| EP | | 1325962 A1 | 7/2003 |
| EP | | 1550462 A1 | 7/2005 |
| EP | | 1276497 B1 | 11/2005 |
| EP | | 1872787 A1 | 1/2008 |
| EP | | 1660100 B1 | 7/2008 |
| EP | | 1456404 B1 | 9/2010 |
| JP | | H02-149527 A | 6/1990 |
| JP | | H08-127539 A | 5/1996 |
| JP | | 2005-527636 A | 9/2005 |
| WO | WO 1987/006235 | A1 | 10/1987 |
| WO | WO 1992/021402 | A1 | 12/1992 |
| WO | WO 1998/048843 | A1 | 11/1998 |
| WO | WO 1998/054313 | A2 | 12/1998 |
| WO | WO 1999/012935 | A1 | 3/1999 |
| WO | WO 1999/057153 | A1 | 11/1999 |
| WO | WO 2000/074634 | A2 | 12/2000 |
| WO | WO 2001/078761 | A2 | 10/2001 |
| WO | WO 2002/053700 | A2 | 7/2002 |
| WO | WO 2003/004705 | A1 | 1/2003 |
| WO | WO 2003/027313 | A2 | 4/2003 |
| WO | WO 2003/052130 | A2 | 6/2003 |
| WO | WO 2003/101468 | A1 | 12/2003 |
| WO | WO 2004/003166 | A2 | 1/2004 |
| WO | WO 2004/028516 | A2 | 4/2004 |
| WO | WO 2004/078922 | A2 | 9/2004 |
| WO | WO 2005/023273 | A1 | 3/2005 |
| WO | WO 2005/089503 | A2 | 9/2005 |
| WO | WO 2006/092036 | A1 | 9/2006 |
| WO | WO 2006/094916 | A1 | 9/2006 |
| WO | WO 2006/094917 | A2 | 9/2006 |
| WO | WO 2006/119619 | A1 | 11/2006 |
| WO | WO 2008/000549 | A1 | 1/2008 |
| WO | WO 2008/125424 | A1 | 10/2008 |
| WO | WO 2009/012237 | A1 | 1/2009 |
| WO | WO 2009/126310 | A2 | 10/2009 |
| WO | WO 2012/063272 | A1 | 5/2012 |
| WO | WO 2013/190582 | A1 | 12/2013 |
| WO | WO 2016/083297 | A1 | 6/2016 |
| WO | WO 2019/028340 | A1 | 2/2019 |

OTHER PUBLICATIONS

Abdalla, S.A. et al., "Prognostic relevance of microvessel density in colorectal tumours," Oncology Reports, vol. 6, Apr. 16, 1999, pp. 839-842.

Akaogi, Jun, et al. "Role of PGE2 and EP Receptors in the Pathogenesis of Rheumatoid Arthritis and as a Novel Therapeutic Strategy." E Endocrine, Metabolic & Immune Disorders—Drug Targets (Formerly Current Drug Targets—Immune, Endocrine & Metabolic Disorders) (2006); 6(4): 383-394.

Albini, A. et al., "A Rapid in Vitro Assay for Quantitating the Invasive Potential of Tumor Cells," American Association for Cancer Research, vol. 47, Jun. 15, 1987, pp. 3239-3245.

Algire, G., "An Adaptation of the Transparent-Chamber Technique to the Mouse," Journal of the National Cancer Institute, vol. 4, No. 1, Aug. 1943, 11 pages.

Andersen, N.F. et al., "Syndecan-1 and angiogenic cytokines in multiple myeloma: correlation with bone marrow angiogenesis and survival," British Journal of Haematology, 2004, vol. 128, pp. 210-217.

Arauz-Pacheco, C. et al., "The treatment of hypertension in adult patients with diabetes," Diabetes Care, vol. 25, No. 1, Jan. 2002, pp. 134-147.

Argoff, C.E. et al., "Diabetic Peripheral Neuropathic Pain: Clinical and Quality-of-Life Issues," Mayo Clinic Proceedings, Supplement, Apr. 2006, vol. 81, No. 4, 34 pages.

Becker et al., "Organikum: organisch-chemisches grundpraktikum" 1990, Deutscher Verlag der Wissenschaften, Berlin, with Google translation, 3 pages.

Belcaro, G. et al., "Fibrinolytic Enhancement in Diabetic Microangiopathy with Defibrotide," Angiology, The Journal of Vascular Diseases, vol. 43, No. 10, Oct. 1992, pp. 793-800.

Belcaro, G. et al., "Laser Doppler Flowmetry and Transcutaneous Oximet Evaluation in Microangiopathic Diabetic Patients Treated with Defibrotide," Current Therapeutic Research, vol. 46, No. 5, May 1989, pp. 726-732.

Benimetskaya et al., "Angiogenesis alteration by defibrotide: implications for its mechanism of action in severe hepatic veno-occlusive disease," Blood, vol. 112, No. 10, Nov. 15, 2008, pp. 4343-4352.

Berti, F. et al., "Effects of defibrotide on prostacyclin release from isolated rabbit kidneys and protection from post-ischemic acute renal failure in vivo," Eicosanoids, vol. 4, 1991, pp. 209-215.

Bianchi, G. et al., "Defibrotide, a Prostacyclin Releasing Agent, Protects the Rabbit Kidney from Acute Failure," Advances in Prostaglandin, Thromboxane, and Leukotriene Research, vol. 21, 1990, pp. 711-714.

Biedermann, B.C., "Vascular endothelium and graft-versus-host-disease," Best Practice & Research Clinical Haematology, vol. 21(2): 129-138, 2008.

Bonomini, V. et al., "Effect of a new antithrombotic agent (defibrotide) in acute renal failure due to thrombotic microangiopathy," Nephron, vol. 40, No. 2, 1985, pp. 195-200.

Bonomini, V. et al., "Use of Defibrotide in Renal Transplantation in Man," Haemostasis, vol. 16, Supp. 1, 1986, pp. 48-50.

Bostwick, D.G. et al., "Microvessel density in prostate cancer: prognostic and therapeutic utility," Seminars in Urologic Oncology, vol. 16, No. 3, Aug. 1998, pp. 118-123.

Brenchley, "Antagonising angiogenesis in rheumathoid arthritis," Annals of the Rheumatic Diseases, vol. 60, 2001, pp. 71-74.

Budavari, S. et al. (eds.), The Merck Index, Twelfth Edition, Merck & Co., Inc., Whitehouse Station, NJ, p. 484 (1996).

Burra, P. et al., "Warm Hepatic Ischemia in Pigs: Effects of L-Arginine and Oligotide Treatment," Journal of Investigative Surgery, vol. 14, 2001, pp. 303-312.

Cao, Y., "Tumor angiogenesis and therapy," Biomedicine & Pharmacotherapy, vol. 59, 2005, pp. S340-S343.

Carlo-Stella, C. et al. "Defibrotide significantly enhances peripheral blood progenitor cell mobilization induced by recombinant human granulocyte colony-stimulating factor (rhG-CSF)." Blood. Vol. 96. No. 11. Abstract #2374, 2000, p. 553a, 2 pages.

Carlo-Stella, C. et al., "Defibrotide in Combination with Granulocyte Col Significantly Enhances the Mobilization of Primitive and Committed Perip Cells in Mice," Cancer Research, vol. 62, Nov. 1, 2002, pp. 6152-6157.

Chalandon, Y., et al., "Prevention of Veno-Occlusive Disease with Defibrotide after Allogeneic Stem Cell Transplantation." Biology of Blood and Marrow Transplantation (2004); 10: 347-354.

(56) References Cited

OTHER PUBLICATIONS

Chapter II Demand for related International Application No. PCT/EP2007/054633, dated Apr. 9, 2008, 10 pages.
Chopra et al., "Defibrotide for the treatment of hepatic veno-occlusive disease: results of the European compassionate-use study," British Journal of Haemotology 111:1122-1129, 2000.
Coccheri et al. "Defibrotide," Cardiovascular Drug Reviews, vol. 9:172-196, 1991.
Coccheri, S. et al., "Defibrotide as a Possible Anti-Ischemic Drug," Seminars in Thrombosis and Hemostasis, vol. 22, Supp. 1, 1996, pp. 9-14.
Comandella, M.G. et al., "Functional and morphological effects of defibrotide on renal ischema," Research in Experimental Medicine, vol. 193, 1993, pp. 65-71.
Conde-Knape, K. et al., "Heparan sulfate proteoglycans in experimental models of diabetes: a role for perlecan in diabetes complications," Diabetes/Metabolism Research and Reviews, vol. 17, 2001, pp. 412-421.
Copelan, E.A. et al., "Hematopoietic Stem-Cell Transplantation," N Engl. J. Med. 354:17, Apr. 27, 2006, pp. 1813-1826.
Coppell, J.A. et al., "Hepatic Veno-Occlusive Disease following Stem Cell Transplantation: Incidence, Clinical Course, and Outcome," Biol. Blood Marrow Transplant (2010) 16, pp. 157-168.
Corbacioglu, S. et al., "Defibrotide for Prophylaxis of Hepatic Veno-Occlusive Disease in Paediatric Haemopoietic Stem-Cell Transplantation: An Open-Label, Phase 3, Randomised Controlled Trial," Lancet 379:1301-1309, 2012.
Corbacioglu et al., "Stem cell transplantation in children with infantile osteopetrosis is associated with a high incidence of VOD, which could be prevented with defibrotide," Bone Marrow Transplantation (2006) 38, 547-553.
Corsi, M. et al., "Antiischaemic effect of defibrotide treatment in rat kidney," Drugs Experimental Clinical Research, vol. 19, No. 6, 1993, pp. 261-265.
Corsi, M. et al., "Possible Role of Defibrotide in Endothelial Cell Protection," International Journal of Tissue Reactions, XV(4), 1993, pp. 157-161.
Craddock, C.F. et al., "Antibodies to VLA4 Integrin Mobilize Long-Term Repopulating Cells and Augment Cytokine-Induced Mobilization in Primates and Mice," Blood, vol. 90, No. 12, Dec. 15, 1997, pp. 4779-4788.
Davi, G. et al., "Effects of Defibrotide on Fibrinolytic Activity in Diabetic Patients with Stable Angina Pectoris," Thrombosis Research, vol. 65, No. 2, 1992, pp. 211-220.
Davis, S. "Insulin, Oral Hypoglycemic Agents, and the Pharmacology of the Endocrine Pancreas," Goodman and Gilman's The Pharmacological Basis of Therapeutics, Chapter 60, Section XII, Hormone sand Hormone Antagonists, McGraw-Hill, 2006, pp. 1613-1645.
De Mestre, A.M. et al., "Regulation of Inducible Heparanase Gene Transcription in Activated T Cells by Early Growth Response 1," The Journal of Biological Chemistry, vol. 278, No. 50, Dec. 12, 2003, pp. 50377-50385.
Dempsey, L. et al., "Heparanase expression in invasive trophoblasts and acute vascular damage," Glycobiology, vol. 10, No. 5, 2000, pp. 467-475.
Denne, J.S., "Sample size recalculation using conditional power," Statist. Med. 2001; 20: pp. 2645-2660.
Dickerson, R.E. et al., "The Anatomy of A-, B- and Z-DNA," Science, vol. 216, No. 4545, 1982, pp. 475-485.
Dignan, F., et al., "Prophylactic defibrotide in allogeneic stem cell transplantation: minimal morbidity and zero mortality from veno-occlusive disease." Bone Marrow Transplantation (2007); 40: 79-82.
Drugbank, "Showing drug card for Defibrotide (DB04932)," retrieved Jan. 21, 2007 from http://www.drugbank.ca/cgi-bin/getCard.cgi?CARD=DB04932.txt, 10 pages.
Echart, C.L. et al., "The fibrinolytic mechanism of defibrotide: effect of defibrotide on plasmin activity," Blood Coagulation and Fibrinolysis 2009, vol. 20, No. 8, pp. 627-634.
Eissner, G. et al., "Defibrotide, a DNA-based drug, modulates endothelial cell function in multiple ways—impact for transplantation and cancer therapy," Vascular Pharmacology, vol. 45, No. 3, Sep. 1, 2006, pp. E152-E153.
Eissner, G. et al., "Fludarabine induces apoptosis, activation, and allogenicity in human endothelial and epithelial cells: protective effect of defibrotide," Blood, Jul. 1, 2002 vol. 100, No. 1, pp. 334-340.
Eissner, G. et al., "Oliogotide, a defibrotide derivative, protects human microvascular endothelial cells against fludarabine-induced activation, damage and allogenicity," Bone Marrow Transplantation, Mar. 2005, 35, pp. 915-920.
Ertault-Daneshpouy, M. et al., "Pericapillary hemorrhage as criterion of severe human digestive graft-versus-host disease," Blood, Jun. 15, 2004, vol. 103, No. 12, pp. 4681-4684.
Esau, Christine C. et al., "Therapeutic potential for microRNAs," Advanced Drug Delivery Reviews, vol. 59, 2007, pp. 101-114.
European Pharmacopoeia 5.0, 5.3 Statistical Analysis, pp. 475-504 (2005), 30 pages.
Falanga, A. et al., "Defibrotide reduces procoagulant activity and increases fibrinolytic properties of endothelial cells," Leukemia (2003); 17(8): 1636-1642.
Fernandez Pujol, B. et al., "Dendritic cells derived from peripheral monocytes express endothelial markers and in the presence of angiogenic growth factors differentiate into endothelial-like cells," European Journal of Cell Biology, vol. 80, Issue 1, 2001, pp. 99-110.
Ferrara, J.L.M. et al., "Graft-versus-host disease," Lancet 2009: vol. 373, May 2, 2009, pp. 1550-1561.
Ferrero, M.E. et al., "Efficacy of Defibrotide Treatment in Favoring the Function of the Grafted Heart and Kidney in Rats," Transplantation Proceedings, vol. 26, No. 1, Feb. 1994, pp. 251-252.
Ferrero, M.E. et al., "Prostacyclin Release from Endothelial Cells, Induced by Defibrotide Treatment, Favours the Function of Grafted Rat Hearts and Kidneys," International Journal of Tissue Reactions, XIII 4,1991, pp. 215-218.
Folkman, J. et al., "Isolation of a tumor factor responsible for angiogenesis," Journal of Experimental Medicine, vol. 133, Issue 2, Feb. 1, 1971, pp. 275-288.
Folkman, J. et al., "Switch to the Angiogenic Phenotype during Tumorigenesis," Princess Takamatsu symposia, Jan. 1991, Boca Raton, pp. 339-347.
Fong, D.S. et al., "Diabetic Retinopathy," Diabetes Care, vol. 27, No. 10, Oct. 2004, pp. 2540-2553.
Fontanini, G. et al., "Microvessel count predicts metastatic disease and survival in non-small cell lung cancer," Journal of Pathology, vol. 177, 1995, pp. 57-63.
Frasca, G.M. et al., "Defibrotide Treatment and Disease Progression in Patients with IgA Nephropathy and Impaired Renal Function at Diagnosis," Clinical Drug Investigation, vol. 13, Issue 4, Apr. 1997, pp. 185-191.
Frasca, G.M. et al., "Effects of defibrotide treatment in patients with IgA nephropathy and reduced renal function," Nephrology Dialysis Transplantation, vol. 11, No. 2, 1996, pp. 392-393.
Friberger, P. et al., "Methods for determination of plasmin, antiplasmin and plasminogen by means of substrate S-2251," Haemostasis, 7:138-145 (1978).
Gharib et al., "Venous occlusive disease in children," Thrombosis Research, vol. 118: 27-38, 2006.
Giraud-Panis, M-J. et al., "Transplatin-modified oligonucleotides as modulators of gene expression," Pharmacology & Therapeutics, vol. 85, 2000, pp. 175-181.
Goldshmidt, O. et al., "Cell surface expression and secretion of heparanase markedly promote tumor angiogenesis and metastasis," Proceedings of the National Academy of Sciences, vol. 99, No. 15, Jul. 23, 2002, pp. 10031-10036.
Guba, M. et al., "Rapamycin induces tumor-specific thrombosis via tissue factor in the presence of VEGF," Blood, vol. 105, Jun. 1, 2005, pp. 4463-4469.
Guba, M. et al., "Rapamycin inhibits primary and metastatic tumor growth by antiangiogenesis: involvement of vascular endothelial growth factor," Nature Medicine, vol. 8, No. 2, Feb. 2002, pp. 128-135.

(56) References Cited

OTHER PUBLICATIONS

Gura, "Systems for Identifying New Drugs are Often Faulty," Science, vol. 278, Nov. 7, 1997, pp. 1041-1042.
Gulati et al., "Parenteral Drug Delivery: A Review," Recent Patents on Drug Delivery & Formulation 2011, 5, 133-145.
Guvakova, M.A. et al., "Phosphorothioate oligodeoxynucleotides bind to basic fibroblast growth factor, inhibit its binding to cell surface receptors, and remove it from low affinity binding sites on extracellular matrix," The Journal of Biological Chemistry, vol. 278, No. 6, Feb. 10, 1995, pp. 2620-2627.
Hames, B.D. et al., "Nucleic Acid Hybridisation," Practical Approach Series, IRL Press, Oxford, 1985, 141 pages.
Han, J. et al., "Endothelial cell injury by high glucose and heparanase is prevented by insulin, heparin and basic fibroblast growth factor," Cardiovascular Diabetology, Aug. 9, 2005, vol. 4, Issue 12, pp. 1-12.
Hanahan, D. et al., "Patterns and emerging mechanisms of the angiogenic switch during tumorigenesis," Cell, vol. 85, Aug. 9, 1996, pp. 353-364.
Hasan, J. et al. "Intra-tumoural microvessel density in human solid tumours," British Journal of Cancer, vol. 86, 2002, pp. 1566-1577.
Hazlehurst, L.A. et al., "Adhesion to fibronectin via b1 integrins regulate p27 kip1 levels and contributes to cell adhesion mediated drug resistance (CAM-DR)," Oncogene, vol. 19, 2000, pp. 4319-4327.
Helmlinger, G. et al., "Interstitial pH and p02 gradients in solid tumors in vivo: high-resolution measurements reveal a lack of correlation," Nature Medicine, vol. 3, No. 2, Feb. 1997, pp. 177-182.
Hershkoviz, R. et al., "Differential effects of polysulfated polysaccharide on experimental encephalomyelitis, proliferation of autoimmune T cells, and inhibition of heparanase activity," Journal of Autoimmunity, vol. 8, No. 5, Oct. 1995, pp. 741-750. Abstract Only.
Imaginis.com, Centre for Women's Health, "Breast Health, Breast Cancer Glossary of Medical Terms" Retrieved from http://www.imaginis.com/glossary/breast-cancer-glossary-of-medical-terms-- 11, date unknown, 4 pages.
International Application No. PCT/IT2012/000193, International Preliminary Reporton Patentability, dated Dec. 23, 2014, 8 pages.
International Application No. PCT/IT2012/000193, International Search Report and Written Opinion, dated Nov. 27, 2012, 12 pages.
International Preliminary Report on Patentability for International Application No. PCT/EP2015/077355, dated May 30, 2017, 7 pages.
International Preliminary Report on Patentability for related International Application No. PCT/EP2004/009723, dated May 31, 2005, 7 pages.
International Preliminary Report on Patentability for related International Application No. PCT/EP2006/060304, dated Jun. 8, 2007, 7 pages.
International Preliminary Report on Patentability for related International Application No. PCT/EP2007/054633, dated Sep. 11, 2008, 7 pages.
International Preliminary Report on Patentability for related International Application No. PCT/EP2008/053461, dated Oct. 20, 2009, 11 pages.
International Preliminary Report on Patentability for related International Application No. PCT/EP2006/060306, dated Sep. 12, 2007, 6 pages.
International Preliminary Report on Patentability for related International Application No. PCT/IT2010/000451, dated May 14, 2013, 5 pages.
International Preliminary Report on Patentability for related International Application No. PCT/EP2009/053002 dated Sep. 21, 2010, 7 pages.
International Search Report and Written Opinion for International Application No. PCT/EP2015/077355, dated Jan. 22, 2016, 10 pgs.
International Search Report and Written Opinion for related International Application No. PCT/EP2004/009723, dated Dec. 22, 2004, 12 pages.
International Search Report and Written Opinion for related International Application No. PCT/EP2006/060304 dated Apr. 8, 2006, 8 pages.
International Search Report and Written Opinion for related International Application No. PCT/EP2006/060306 dated Sep. 25, 2006, 8 pages.
International Search Report and Written Opinion for related International Application No. PCT/EP2007/054633 dated Aug. 24, 2007, 9 pages.
International Search Report and Written Opinion for related International Application No. PCT/EP2008/053461 dated Oct. 9, 2008, 15 pages.
International Search Report and Written Opinion for related International Application No. PCT/EP2009/053002 dated Jun. 5, 2009, 11 pages.
International Search Report for International Application No. PCT/EP2002/013371, dated Jul. 23, 2003, 4 pgs.
International Search Report for International Application No. PCT/IT2010/000451, dated Jun. 22, 2011, 2 pgs.
International Search Report and Written Opinion for International Application No. PCT/US2018/045152, dated Dec. 5, 2018, 13 pages.
Irony-Tur-Sinai, M. et al., "A synthetic heparin-mimicking polyanionic compound inhibits central nervous system inflammation," Journal of the Neurological Sciences, Jan. 2003, vol. 206, No. 1, Jan. 15, 2003, pp. 49-57. Abstract Only.
Isaji, M. et al., "Tranilast inhibits the proliferation, chemotaxis and tube formation of human microvascular endothelial cells in vitro and angiogenesis in vivo," British Journal of Pharmacology, vol. 122, 1997, pp. 1061-1066.
Japanese Patent Application No. 2013-538335, Official Notice of Rejection dated Sep. 24, 2014 (with English translation), 6 pages.
Jeffery, C.J. et al., "The *Escherichia coli* aspartate receptor: sequence specificity of a transmembrane helix studied by hydrophobic-biased random mutagenesis," Protein Engineering, vol. 12, No. 10, 1999, pp. 863-871.
Kainz, C. et al., "Prognostic value of tumour microvessel density in cancer of the uterine cervix stage IB to IIB," Anticancer Research, vol. 15, No. 4, Jul.-Aug. 1995; pp. 1549-1551.
Kaiser, "First Pass at Cancer Genome Reveals Complex Landscape," Science, vol. 313, Sep. 8, 2006, p. 1370.
Karlsson et al., "N-acetyl-L-cysteine promotes T-cell mediated immunity in allogeneic settings in vivo and in vitro," Oral Session 11: Immunotherapy/Experimental Graft-Versus-Host-Disease, 35th Annual Meeting of the European Group for Blood and Marrow Transplantation, Göteborg, Sweden, Mar. 31, 2009.
Kaushansky, K. et al., "Hematopoietic Growth Factors: Understanding Functional Diversity in Structural Terms," The Journal of The American Society of Hematology, Blood, vol. 82, No. 11, Dec. 1, 1993, pp. 3229-3240.
Kelland, "'Of mice and men': values and liabilities of the athymic nude mouse model in anticancer drug development," European Journal of Cancer, vol. 40, 2004, pp. 827-836.
Kerbel, "Human tumor Xenografts as Predictive Preclinical Models for Anticancer Drug Activity in Humans," Cancer Biology & Therapy, vol. 2, No. 4, Suppl. 1, Jul./Aug. 2003, pp. S134-S139.
Khaled, Z. et al., "Multiple mechanisms may contribute to the cellular anti-adhesive effects of phosphorothioate oligodeoxynucleotides," Nucleic Acids Research, vol. 24, No. 4, 1996, pp. 737-745.
Kochar, D.K. et al., "Sodium valproate for painful diabetic neuropathy: a randomized double-blind placebo-controlled study," QJM: An International Journal of Medicine, vol. 97, 2004, pp. 33-38.
Koehl, G.E. et al., "Defibrotide an endothelium protecting and stabilizing drug, has an anti-angiogenic potential in vitro and in vivo," Cancer Biology & Therapy, vol. 6, No. 5, May 2007, pp. 686-690.
Kojima, S. et al., "Enhancement of plasminogen activator activity in cultured endothelial cells by granulocyte colony-stimulating factor," Journal of Cellular Physiology, vol. 138, Jan. 1989, pp. 192-196. Abstract Only.
Kornblum, Noah, et al. "Defibrotide, a polydisperse mixture of single-stranded phosphodiester oligonucleotides with lifesaving activ-

(56) References Cited

OTHER PUBLICATIONS ity in severe hepatic veno-occlusive disease: clinical outcomes and potential mechanisms of action." Oligonucleotides (2006); 16.1:105-114.
Lee, S.J. et al., "Recognizing and Managing Chronic Graft-Versus-Host Disease," American Society of Hematology (2008) pp. 134-141.
Levidiotis, V. et al., "A synthetic heparanase inhibitor reduces proteinuria in passive heymann nephritis," Journal of the American Society of Nephrology, vol. 15, 2004, pp. 2882-2892.
Levidiotis, V. et al., "Heparanase inhibition reduces proteinuria in a model of accelerated anti-glomerular basement membrane antibody disease," Nephrology, vol. 10, 2005, pp. 167-173.
Levidiotis, V. et al., "Heparanase is involved in the pathogenesis of proteinuria as a result of glomerulonephritis," Journal of the American Society of Nephrology, vol. 15, 2004, pp. 68-78.
Levidiotis, V. et al., "Increased expression of heparanase in puromycin aminonucleoside nephrosis," Kidney International, vol. 60, 2001, pp. 1287-1296.
Li, Q., et al., "Involvement of caspase-3 and p38MAPK in allogeneic CD8+T cell-induced apoptosis of vascular endothelial cells," Chinese Journal of Pathophysiology, 2009, vol. 25, Issue 9, Published Sep. 15, 2009, pp. 1671-1675 (English Abstract).
Maeshima, Y. et al., "Identification of the Anti-angiogenic Site within Vascular Basement Membrane-derived Tumstatin," The Journal of Biological Chemistry, vol. 276, No. 18, May 4, 2001, pp. 15240-15248.
Marni, A. et al. "Anti-ischemic effect of oligopeptide treatment in rat kidney: comparison with the effect of nifedipine and isosorbide dinitrate," Transplantation Proceedings, vol. 28, No. 1, Feb. 1996, pp. 301-303.
Marni, A. et al., "Protection of Kidney from Postischemic Reperfusion Injury in Rats Treated with Defibrotide," Transplantation Proceedings, vol. 22, No. 5, Oct. 1990, pp. 2226-2229.
Maxhimer, J.B. et al., "Heparanase-1 gene expression and regulation by high glucose in renal epithelial cells," Diabetes, Jul. 2005, vol. 54, pp. 2172-2178.
McDonald, G.E. et al., "Venocclusive Disease of the Liver after Bone Marrow Transplantation: Diagnosis, Incidence, and Predisposing Factors," Hepatology vol. 4, No. 1, 1984, pp. 116-122.
McDonald, G.E. et al., "Veno-occlusive Disease of the Liver and Multiorgan Failure after Bone Marrow Transplantation: A Cohort Study of 355 Patients," Annals of Internal Medicine, 1993; 118:255-267.
Mitsiades, C.S. et al., "Defibrotide (DF) Targets Tumor-Microenvironmental Interactions and Sensitizes Multiple Myeloma and Solid Tumor Cells to Cytotoxic Chemotherapeutics," Blood (ASH Annual Meeting Abstracts), 2004, vol. 104, Abstract 286.
Mitsiades, C.S. et al., "Preclinical Studies in Support of Defibrotide for the Treatment of Multiple Myeloma and Other Neoplasias," Clin Cancer Res 2009;15(4), Feb. 15, 2009, pp. 1210-1221.
Mitsiades, C.S., "Defibrotide (DF) an Orally Bioavailable Modulator of Myeloma Tumor-Microenvironment Interactions: Molecular Sequetae and Clinical Implications," Blood (ASH Annual Meeting Abstracts), 2006 108: Abstract 3523, Poster Board #—Session: 752-III.
Mitsiades, C.S., et al., "Defibrotide (DF) has anti-neoplastic activity against multiple myeloma: Clinical implications for the incorporation of DF in cytotoxic chemotherapeutic regimes," Blood, vol. 102, No. 11, Nov. 16, 2003, p. 693a, Abstract 2567, Poster Board #—Session: 738-II.
Mondesire, W. et al., "Targeting Mammalian Target of Rapamycin Synergisticallly Enhances Chemotherapy-Induced Cytotoxicity in Breast Cancer Cells," Clinical Cancer Research, vol. 10, Oct. 2004, pp. 7031-7042.
Morabito, A. et al., "Antiangiogenic strategies, compounds, and early clinical results in breast cancer," Critical Reviews in Oncology/Hematology, vol. 49, 2004, pp. 91-107.

Murohara, T. et al., "Cardioprotective actions of oligopeptide, a single stranded polydeoxyribunucleotide complex, in myocardial ischaemia and reperfusion injury," British Journal of Pharmacology, vol. 117, 1996, pp. 1000-1008.
National Library of Medicine, "Defibrotide"—Medical Subject Heading, 2009 MeSH, MeSH Supplementary Concept Data.
Niada, R., et al., "PGI2-generation and antithrombotic activity of orally administered defibrotide," Pharmacological Research Communications, vol. 14, Issue 10, Nov. 1982, pp. 949-957. Abstract Only.
Nieuwenhuizen, W. et al., "Fluorogenic substrates for sensitive and differential estimation of urokinase and tissue plasminogen activator," Haemostasis, 7:146-149 (1978).
Orsino, A. et al., "Childhood acute myelomonocytic leukemia (AML-M4) presenting as catastrophic antiphospholipid antibody syndrome," Journal of Pediatric Hematology/Onocology, vol. 26, No. 5, May 2004, pp. 327-330.
Osterberg and See, "Toxicity of Excipients—A Food and Drug Administration Perspective," International Journal of Toxicology, 2003, 22:377-380.
Ostrovsky, O. et al., "Genetic variations in the heparanase gene (HPSE) associate with increased risk of GVHD following allogeneic stem cell transplantation: effect of discrepancy between recipients and donors." Blood, Mar. 18, 2010, vol. 115, No. 11, pp. 2319-2328.
Palmer, K.J., et al., "Defibrotide A Review of its Pharmacodynamic and Pharmacokinetic Properties, and Therapeutic Use in Vascular Disorders," Drugs, vol. 45, No. 2, 1993, pp. 259-294.
Parish, C.R. et al., "Heparanase: a key enzyme involved in cell invasion," Biochimica et Biophysica Acta, vol. 1471, 2001, M99-M108.
Parish, C.R. et al., "Treatment of central nervous system inflammation with inhibitors of basement membrane degradation," Immunology and Cell Biology, vol. 76, No. 1, Feb. 1998, pp. 104-113.
Pellegatta, F. et al., "The anti-ischemic drugs defibrotide and oligotide analogously inhibit leukocyte-endothelial cell adhesion in vitro," Transplant International, vol. 9, Suppl. 1, 1996, pp. S420-S424.
Persengiev, S.P. et al., "Nonspecific, concentration-dependent stimulation and repression of mammalian gene expression by small interfering RNAs (siRNAs)," RNA, vol. 10, 2004, pp. 12-18.
Pescador, R. et al., "An Integrated View of the Activities of Defibrotide," Seminars in Thrombosis and Hemostasis, vol. 22, Suppl. 1, 1996, pp. 71-75.
Plaut, "p-Nitrobenzyl p-Toluenesulfonyl-L-Arginine: A Chromogenic Substrate for Thrombin, Plasmin, and Trypsin," Haemostasis, vol. 7:105-108, 1978.
Podar, K. et al., "The pathophysiologic role of VEGF in hematologic malignancies: therapeutic implications," Blood, vol. 105, No. 4, Feb. 15, 2005, pp. 1383-1395.
Porta et al., "High-Performance Liquid Chromatography Determination of Polydeoxyribonucleotides in Plasma: Its Application to the Determination of Defibrotide's Pharmacokinetics in the Rabbit," Analytical Biochemistry, vol. 204:143-146, 1992.
Prino, G. et al., Indagini preliminari sull'attivita fibrinolitica, nell'animale E nell'uomo, di una nuova sostanza presente in diversi organi animali, Simposio Internazionale, La Ricerca Scientifica Nell'Industria Farmaceutica in Italia, Risultati e Ruolo Internazionale, Roma, Oct. 2-4, 1975 (with English summary), 7 pages.
Prosper, F. et al., "Mobilization and Homing of Peripheral blood Progenitors Is Related to Reversible Downregulation of alpha4Beta1 Integrin Expression and Function," The American Society for Clinical Investigation, Inc., vol. 101, No. 11, Jun. 1998, pp. 2456-2467.
PureLink Brochure, "Nucleic Acid Purification" Invitrogen, 2007, 8 pages.
Ranieri et al., "Defibrotide in the treatment of Raynaud's phenomenon in patients with progressive systemic sclerosis or essential mixed cryoglobulinemia," Current Therapeutic Research, vol. 53:48-58, 1993.
Richardson et al., "Defibrotide for the Treatment of Severe Hepatic Veno-Occlusive Disease and Multiorgan Failure after Stem Cell Transplantation: A Multicenter, Randomized, Dose-Finding Trial," Biol Blood Marrow Transplant 16:1005-1017, 2010.

(56) References Cited

OTHER PUBLICATIONS

Richardson et al., "Defibrotide (DF) in the Treatment of Severe Hepatic Veno-Occlusive Disease (VOD) with Multi-Organ Failure (MOF) Following Stem Cell Transplantation (SCT): Results of a Phase 3 Study Utilizing a Historical Control," Blood, vol. 114, 22, Abstract 654, 2009.

Richardson et al., "Multi-institutional use of defibrotide in 88 patients after stem cell transplantation with severe veno-occlusive disease and multisystem organ failure: response without significant toxicity in a high-risk population and factors predictive of outcome," Blood 100(13):4337-4343, 2002.

Richardson, P.G. et al., "Treatment of severe veno-occlusive disease with defibrotide: compassionate use results in response without significant toxicity in a high-risk population," Blood, vol. 92, No. 3, Aug. 1, 1998, pp. 737-744.

Rowlings, P.A. et al., "IBMTR Severity Index for grading acute graft-versus-host disease: retrospective comparison with Glucksberg grade," British Journal of Haematology, 1997, 97, pp. 855-864.

Ruutu, T. et al., "Diagnostic criteria for hematopoietic stem cell transplant-associated microangiopathy: results of a consensus process by an International Working Group," haematologica/the hematology journal, 2007; 92(1):95-100.

Schroder, "Defibrotide protects endothelial cells, but not L929 tumour cells, from tumour necrossis factor-alpha-mediated cytotoxicity," Journal of Pharmacy and Pharmacology, vol. 47, 1995, pp. 250-252.

Simizu, S. et al., "Heparanase as a molecular target of cancer chemotherapy," Cancer Science, vol. 95, No. 7, Jul. 2004, pp. 553-558.

Stanford Health Care ECL sheet: 1 page total. Retrieved from the internet Jul. 10, 2016, 1 page.

Staton, C.A. et al., "Current methods for assaying angiogenesis in vitro and in vivo," International Journal of Experimental Pathology, vol. 85, 2004, pp. 233-248.

Stephan, S. et al., "Effect of Rapamycin Alone and in Combination with Antiangiogenesis Therapy in an Orthotopic Model of Human Pancreatic Cancer," American Association for Cancer Research, 2004.

Sun, H.C. et al., "Microvessel density of hepatocellular carcinoma: its relationship with prognosis," Journal of Cancer Research and Clinical Oncology, vol. 125, 1999, pp. 419-426.

Tai, BC et al., "Competing risks analysis of patients with osteosarcoma: a comparison of four different approaches," Statis. Med. 2001; 20:661-684.

Tamsma, J.T. et al., "Expression of glomerular extracellular matrix components in human diabetic nephropathy: decrease of heparan sulphate in the glomerular basement membrane," Diabetologia, vol. 37, 1994, pp. 313-320.

Trichon, B.H. et al., "Acute coronary syndromes and diabetes mellitus," Diabetes and Vascular Disease Research, vol. 1, Issue 1, May 2004, pp. 23-32.

Van Den Born, J. et al., "Distribution of GBM heparan sulfate proteoglycan core protein and side chains in human glomerular diseases," Kidney International, vol. 43, 1993, pp. 454-463.

Van't Veer, L.J. et al., "Gene expression profiling predicts clinical outcome of breast cancer," Nature, vol. 415, Jan. 31, 2002, pp. 530-536.

Verheul, H.M.W. et al., "Are tumours angiogenesis-dependent?," Journal of Pathology, vol. 202, 2004, pp. 5-13.

Vermuelen, M. et al., "Role of Adhesion Molecules in the Homing and Mobilization of Murine Hematopoietic Stem and Progenitor Cells," Blood, vol. 92, No. 3, Aug. 1, 1998, pp. 894-900.

Vingolo, E.M., et al., "Treatment of nonproliferative diabetic retinopathy with Defibrotide in noninsulin-dependent diabetes mellitus: A pilot study," Acta Opthalmologica, vol. 77, 1999, pp. 315-320.

Vlodavsky, I. et al., "Mammalian heparanse: Gene cloning, expression and function in tumor progression and metastasis," Nature Medicine, vol. 5, No. 7, Jul. 1999, pp. 793-802.

Vlodavsky, I. et al., "Molecular properties and involvement of heparanase in cancer metastasis and angiogenesis," The Journal of Clinical Investigation, vol. 108, No. 3, Aug. 2001, pp. 341-347.

Voskoglou-Nomikos, T. et al., "Clinical Predictive Value of the in Vitro Cell Line, Human Xenograft, and Mouse Allograft Preclinical Cancer Models," Clinical Cancer Research, vol. 9, Sep. 15, 2003, pp. 4227-4239.

Weidner, N. et al., "Tumor angiogenesis: a new significant and independent prognostic indicator in early-stage breast carcinoma," Journal of the National Cancer Institute, vol. 84, No. 24, Dec. 16, 1992, pp. 1875-1887.

Written Opinion for International Application No. PCT/IT2010/000451, dated Jun. 22, 2011, 4 pgs.

Xiangming, C. et al., "Angiogenesis as an unfavorable factor related to lymph node metastasis in early gastric cancer," Annals of Surgical Oncology, vol. 5, No. 7, 1998, pp. 585-589.

Yang, Y. et al., "Heparanase promotes the spontaneous metastasis of meloma cells to bone," Blood, vol. 105, No. 3, Feb. 1, 2005, pp. 1303-1309.

EUGLOBULIN-BASED METHOD FOR DETERMINING THE BIOLOGICAL ACTIVITY OF DEFIBROTIDE

This application is a continuation of U.S. application Ser. No. 17/396,028, filed Aug. 6, 2021, which is a continuation of U.S. application Ser. No. 16/816,741, filed Mar. 12, 2020, now U.S. Pat. No. 11,085,043, which is a continuation of U.S. application Ser. No. 15/844,801 filed Dec. 18, 2017, now abandoned, which is a continuation of U.S. application Ser. No. 14/408,272 filed Dec. 15, 2014, now U.S. Pat. No. 9,902,952, and which is a 371 of international PCT/IT2012/000193, filed Jun. 22, 2012, each of which is herein incorporated by reference in its entirety.

The present invention relates to a method for determining the biological activity of defibrotide and, more especially, relates to an indirect enzymatic method for determining the biological activity of defibrotide.

TECHNICAL FIELD OF THE INVENTION

Defibrotide (Merck Index, 1996, no. 2915) is a substance of natural origin which is obtained by extraction from animal organs and which is constituted by the sodium salt of polydeoxyribonucleotides having a low molecular weight. Defibrotide has been the subject of numerous pharmacological investigations which have suggested that it be applied in therapy as an anti-thrombotic agent (U.S. Pat. No. 3,829,567).

In addition, defibrotide has also been used successfully in the treatment of peripheral arteriopathies, in acute renal insufficiency (U.S. Pat. No. 4,694,134) or in acute myocardial ischaemia (U.S. Pat. No. 4,693,995).

Defibrotide is currently undergoing clinical trials to be used for the treatment and prevention of venous occlusive disease (VOD).

Like other biological substances which are obtained by extraction, defibrotide is also subject to a limited variability of composition which is typical of natural biopolymers. A classical example of this situation is provided by heparin whose variability from batch to batch in terms of chain length, molecular weight, composition, degree of sulphatation, etc. is well known. The consequence of this is that the same amounts by weight of defibrotide could in fact be non-equivalent from the point of view of a specific biological activity.

The process of extraction, isolation and purification cannot per se ensure absolute reproducibility of the product, precisely owing to its intrinsic biopolymeric nature.

However, if well controlled, it is possible to reduce this variability: for that purpose, studies have been made of standardized industrial processes for isolating defibrotide by extraction from organs, such as, for example, that described in U.S. Pat. No. 4,985,552.

The product obtained according to the above-mentioned process is characterized by the determination of some specific physico-chemical parameters, such as, for example, electrophoretic mobility, the coefficient of extinction, optical rotatory power and mass-average relative molecular mass. However, those parameters depend basically on the structure of defibrotide and are not capable of providing information on the biological activity thereof.

As far as we know, the only methods that have been reported to be used hitherto to evaluate the biological activity of defibrotide are the fibrin plate test and the thromboelastographic recording of the euglobulin lysis time [Prino G., Mantovani M., Niada R., Coccheri S., Butti A., Indagini preliminari sull'attivita fibrinolitica, nell'animale e nell'uomo, di una nuova sostanza presente in diversi organi animali, Simposio Internazionale: La ricerca scientifica nell'industria farmaceutica in Italia, Rome, 2-4 Oct. 1975-11 Farmaco, Ed. Prat.) (1969), 24, 552-561] and the method based on plasmin disclosed in U.S. Pat. No. 7,338,777, herein incorporated by reference.

However, the above-mentioned method thromboelastographic recording of the euglobulin lysis time is characterized by considerable experimental complexity, by unsatisfactory reproducibility and precision and, in the specific case of thromboelastographic recording, by a response linearity limited to very restricted concentration ranges.

As to the plasmin-based method, the enzymatic activity of plasmin is normally determined by various standard in vitro tests. One of the most commonly used methods is the determination by spectrophotometry or fluorimetry of the chromogenic or fluorogenic compounds that are freed by the action of plasmin on suitable substrates [Haemostasis, (1978), 7, 138-145]. Peptide substrates having the formula $A_1$-$A_2$-$A_3$-X are generally used in which $A_1$ and $A_2$ are amino acids that are predominantly non-polar, $A_3$ is lysine or arginine and X represents the measurable freed compound, for example para-nitroaniline (pNa) or 2-naphthylamine (NA) [Haemostasis, (1978), 7, 146-149]. In addition to the above-mentioned peptide substrates, success has been achieved using other, simpler, compounds, such as, for example, p-nitrobenzyl-p-toluenesulphonyl-L-arginine [Haemostasis, (1978), 7, 105-108].

The rate at which the compound X is released into the incubation medium is proportional to the activity (Units/mg) of plasmin present in the sample. The method disclosed in U.S. Pat. No. 7,338,777 is thus based on the finding that, in the plasmin-evaluation tests described above, defibrotide increases the rate of release of compound X proportionally to its concentration.

However, such a method is conducted in TRIS buffer without any other plasma/serum activator/inhibitor. Therefore, the procedure does not reflect the physiological condition nor accurately simulates the mechanism of action of defibrotide in vivo.

Hitherto, therefore, no truly valid, precise and reproducible methods have been described and validated for determining the biological activity of defibrotide reflecting in an accurate way the mechanism of action of the product in a complex biological system (in vivo).

We have developed a simple and reliable method for determining the biological activity of defibrotide, which enables the samples obtained by extraction to be controlled and therefore enables medicinal preparations based on defibrotide to be standardized.

The method to which the present invention relates enables the specific biological activity of defibrotide to be determined in comparison with a reference standard with a high degree of precision and accuracy.

DESCRIPTION OF THE INVENTION

Figure 1:
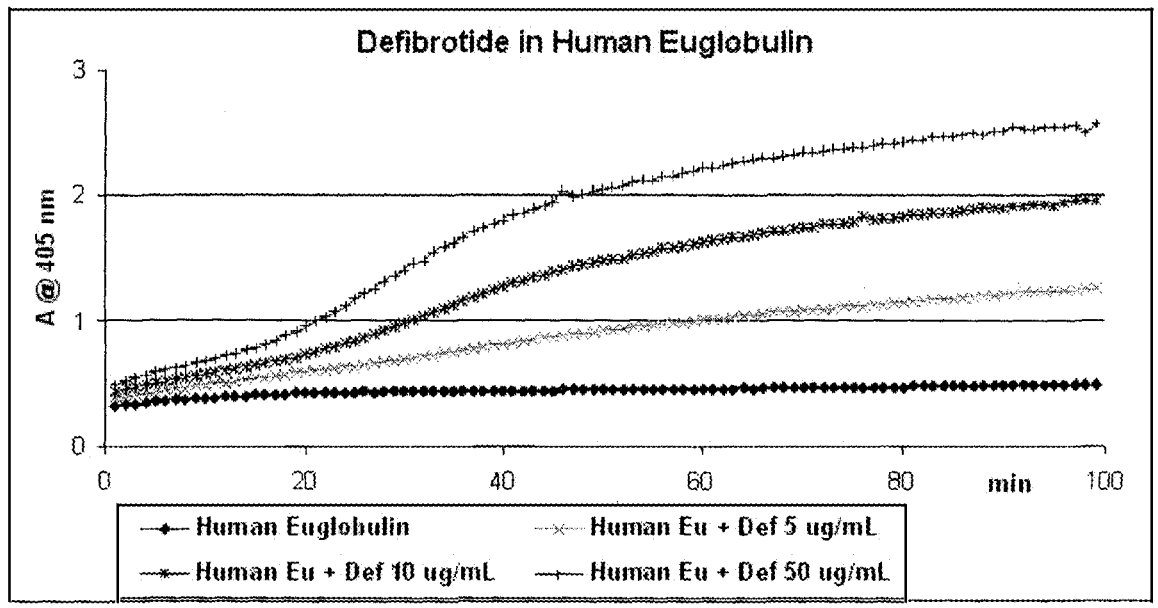
FIG. 1 is a plot showing the kinetics of release of pNA from the substrate S-2251, by means of mammalian euglobulin fraction which is activated and non-activated with defibrotide (concentration 0-50 µg/ml, 0-100 min).

The present invention therefore relates to a method for determining the specific biological activity of samples of defibrotide, which method comprises the steps of:
a) bringing into contact defibrotide, euglobulin and a substrate specific for the plasmin which, by reaction with the plasmin, provides a measurable product and
b) measuring the amount of product formed at successive times.

The method of the invention is an indirect in vitro method for determining the activity of defibrotide, which is based on the functional interactions between defibrotide and euglobulin.

Euglobulin is that fraction of serum globulin that is insoluble in distilled water but soluble in saline solutions.

Euglobulin contains fibrinogen, PAI-1, tissue plasminogen activator (tPA), plasminogen, and to a lesser extent alpha 2-antiplasmin and also factor VIII.

The present inventors have surprisingly found that defibrotide catalyzes the hydrolysis of plasminogen into plasmin. Consequently, when defibrotide is incubated with euglobulin and a substrate specific for plasmin, such as a peptide of formula $A_1$-$A_2$-$A_3$-X as disclosed by Haemostasis, (1978), 7, 138-149, herein incorporated by reference, the rate at which the compound X is released into the incubation medium increases proportionally to the concentration of defibrotide itself.

In other terms, defibrotide catalyzes the hydrolysis of plasminogen contained in euglobulin into plasmin; which plasmin enzymatically reacts with the substrate specific for plasmin, preferably a chromogenic substrate, to provide a measurable product.

The method of the present invention thus further comprises the steps of: c) determining the rate of release of the measurable product during the course of the enzymatic reaction of both a standard sample and a test sample of defibrotide; d) correlating, mathematically and/or graphically, the rate of release with the corresponding defibrotide concentration to obtain the biological activity of the test sample of defibrotide.

The defibrotide sample used for the determination according to the present invention is generally prepared by extraction from organs in accordance with known procedures, such as described, for example, in U.S. Pat. No. 4,985,552 which has already been mentioned and which is also herein incorporated by reference.

A batch of normal industrially manufactured defibrotide was chosen as the reference sample (standard) and was used to prepare the calibration curves in accordance with the method of the present invention.

In general, the present method provides precise and accurate measurements of defibrotide even in the presence of contaminants, such as, for example, RNA, heparin, degraded defibrotide (defibrotide from which purin or pyrimidine has been removed) or ethanol, provided they are in concentrations, generally less than 10% by weight, such as not to impair the system.

In addition to permitting the determination of defibrotide, the method also allows the determination of other biologically equivalent substances derived from defibrotide, such as, for example, deaminated defibrotide or, more simply, defibrotide denatured/degraded by combination of physico-chemical conditions.

The present method is sufficiently sensitive to detect concentrations of defibrotide lower than or equal to 2.5 μg/ml (final concentration in the determination system) and, generally, expresses good correlation up to maximum concentration values higher than or equal to 1000 μg/ml.

The euglobulin used is generally any mammalian euglobulin fraction, such as, for example, bovine, porcine, rabbit or human euglobulin, with a preference for human and bovine euglobuline.

However, although euglobulin fraction is the enzymatic system of choice, the use of other equivalent enzymatic systems, such as, for example, diluted plasma and serum (up to 1:10 with buffers), artificially created or isolated combinations of plasminogen, tPA, uPA, PAI-1&2 alpha 2 antiplasmin and the like enzymatic systems which are chemically and biologically related and have similar functionality, falls within the scope of the present invention.

In the method of the present invention, the substrate for the plasmin may be understood as being any substrate specific for plasmin which, under the conditions of the method, frees a detectable hydrolysis product X.

Depending on the nature of the detectable group X, alternative systems of detection commonly known to the person skilled in the art can be adopted equally well. Spectrophotometric or fluorimetric detection systems are particularly advantageous, especially spectrophotometric systems.

The substrates generally used are ones that are specific for plasminoge-plasmin assay. It is preferable to use peptides of the formula $A_1$-$A_2$-$A_3$-X, in which $A_1$ and $A_2$ are amino acids that are predominantly non-polar, $A_3$ is lysine or arginine and X is the detectable group. Examples of those substrates are Val-Leu-Lys-pNa, Val-Phe-Lys-pNa or pyro-Glu-Phe-Lys-pNa in which the group X detectable by spectrophotometry is para-nitroaniline (pNA). Other suitable substrates, for example Val-Gly-Arg-2NA, contain 2-naphthylamine, which is measurable by fluorimetry. A particularly preferred substrate is the compound H-D-Valyl-L-Leucyl-L-Lysine-p-nitroaniline (H-D-Val-Leu-Lys-pNA).

The specific substrates used for determining defibrotide activity in euglobulin fraction are generally commercially available.

The determination method of the present invention is carried out by placing defibrotide sample in euglobulin solution, at a specific pH and molarity.

In particular, euglobulin fractions obtained from mammalian plasma are reconstituted dissolving and diluting the euglobulin to the original volume of the generating plasma with saline buffer (ex.: the quantity of euglobulin fraction obtained from 10 mL plasma are dissolved and reconstituted to 10 mL with saline buffer at pH between 7 and 8).

However, as regards of the substrate concentrations of from 0.3 to 4 mM, preferably from 2.5 to 3.5 mM and advantageously of 3 mM, are generally used in the case of a chromogenic substrate, while concentrations of from 0.05 to 0.15 mM are used in the case of a fluorogenic substrate.

The determination method of the invention, like other enzymatic methods, is sensitive to the pH of the medium.

In fact, it cannot generally be applied at extreme pH values where the enzymatic system would be inactivated.

It is also preferable for the pH of the medium not to undergo variation at any time during the period when measurements are being taken, and therefore euglobuline fraction is reconstituted with buffer systems selected from those normally used for biological tests. Suitable buffer systems may be, for example, phosphate buffer, citrate buffer or tris(hydroxymethyl)aminomethane hydrochloride and sodium chloride (TRIS-NaCl) buffer. The reconstitution of the euglobuline fraction is preferably carried out with TRIS-NaCl.

In the present method it is usually preferred to maintain the pH of the medium in a range of approximately from 7 to 8, more preferably at approximately 7.4-7.6.

In addition, it is preferred to maintain the concentration of the buffer system in a range of from 10 to 200 mM, preferably at approximately 50 mM. More specifically for the TRIS-NaCl the concentrations should be 50 mM for TRIS and 150 mM for sodium chloride The method of the invention for determining defibrotide biological activity, defibrotide sample solutions is diluted directly into euglobulin fraction, then the chromogenic or fluorogenic substrate is added. In particular, in order to enable the measurements it is preferable to preliminary dilute/dissolve defibrotide in TRIS-NaCl buffer in order to obtain a mother stock solution of both, sample and standard. From the mother stock solutions the sample and the standard are diluted, by serial dilution, into defined volume of euglobulin fraction till the analytical concentration range which is about 1 to 1000 µg/mL of defibrotide An important parameter in the present method of determination is the temperature. It is preferable for the same temperature to be maintained throughout the entire duration of the measurements and for all of the samples determined, both as regards the construction of the reference curves and during the measuring stage. To that end, it is preferable to use temperature controlled apparatus and also, where necessary, it is possible to proceed with several sets of measurements, changing the position of the samples appropriately in order to ensure that the system has maximum thermal homogeneity.

Generally, this method of determination is applied in a temperature range of, for example, from 25 to 40° C., preferably from 35 to 39° C., and even more preferably at 37° C.

According to the present invention, measurement of the concentration of compound X released in the medium by the action of defibrotide starts when all of the reagents have been added and continues for a predetermined time and at a predetermined frequency as a function of the chemical nature of X and of the detection system.

Similarly to other methods of biological determination, the method of the invention also provides for a calibration stage and a measuring stage which are preferably carried out in the same microplate plate in order to reduce as far as possible the incidence of experimental variability.

The calibration stage comprises the acquisition of the absorbance data relating to the samples at known increasing concentrations of defibrotide (standard), the statistical reprocessing of those data and the extrapolation of calibration curves, which express the correlation between the increase in the rate of the enzymatic reaction of the invention and the concentration of defibrotide present in the euglobulin fraction. In the measuring stage, owing to the correlation obtained in the calibration stage, it is possible to determine the unknown biological activities of samples of defibrotide on the basis of the absorbance values measured and processed under the same conditions.

In more detail, the experimental protocol generally provides for the preparation of several samples, both standard and unknown, at various known concentrations of defibrotide. The defibrotide samples are prepared by progressive dilution of the mother solutions in accordance with a predetermined dilution factor.

In the present method, it is preferred to prepare at least 5 concentrations of the standard and 5 concentrations of the sample to be tested, preparing at least 4 replicates for each concentration of the standard and, similarly, for each concentration of the test sample, generally for successive 1:2 dilutions of mother solutions.

Both the standard and test-sample concentrations of defibrotide are generally from 0.1 to 1000 µg/ml.

The concentrations of the test sample are preferably of the same order of magnitude as the concentrations of the standard.

In accordance with the above illustration, the measurements for each concentration are preferably carried out on 1 microplates where the position of each sample, the standard and the test sample, respectively, at corresponding concentration is preferably alternated. According to this scheme for the arrangement of the samples, which is explained in more detail in the experimental part, for each concentration of both standard and test-sample defibrotide, at least 4 absorbance values are measured for each time.

The set of measurements described above are taken at predetermined times, that is to say, first of all at time $t_0$, that is to say, when all of the components have been added, before the enzymatic reaction of the invention has started, and subsequently at precise intervals and for a period of time sufficient to acquire the necessary data.

Preferably, the absorbance measurements are continued up to a maximum of 90 minutes, with readings taken every 1-10 minutes. More advantageously, the readings are taken every minute. The photometric absorbance readings are performed at a wavelength which depends on the nature of the detectable group X freed in the course of the enzymatic hydrolytic reaction. In the specific case in which X is p-NA, the absorbance is measured at 405 nm.

The absorbance readings of the standard and unknown defibrotide samples, known as raw data, generally originate directly from the same apparatus that provides for the reading operation; they are tabulated in such a manner that an absorbance value is expressed for each time and well.

The raw data are then processed, using, for example, the Spread Sheet—Microsoft Excel®. This first processing operation leads to the calculation of the average absorbance and of the associated standard deviation, at each time and for each set of readings, each set comprising at least 4 replicates for each concentration of both standard and test-sample defibrotide.

Further statistical processing of the data is carried out with commercially available software for biological assay determination as described by Finney D J, Statistical Method in Biological Assay, 2nd ed. Ch. Griffin, London and relevant Pharmacopoeias.

To be more precise, according to the present invention, defibrotide biological assay determination can be performed using parallel line model, slope ration model and four-parameter logistic curve models as defined, for example, by the relevant European Pharmacopoeia General text 5.3, Statistical Analysis"

As illustrated in FIG. 1, by placing the time on the abscissa and the absorbance on the ordinate, straight lines will be obtained whose slope "b" will be proportional to the rate of enzymatic reaction: by increasing the concentration of defibrotide, the rate of hydrolysis and, proportionally, the value of "b" will increase. Finally, the slope values, calculated as described above for each set of replicates of standard defibrotide and test-sample defibrotide, are correlated with the concentration of defibrotide to which they relate. Suitable mathematical transformation of the abscissa (i.e. log of defibrotide concentration) can be used in lieu of the real value.

Figure 2:
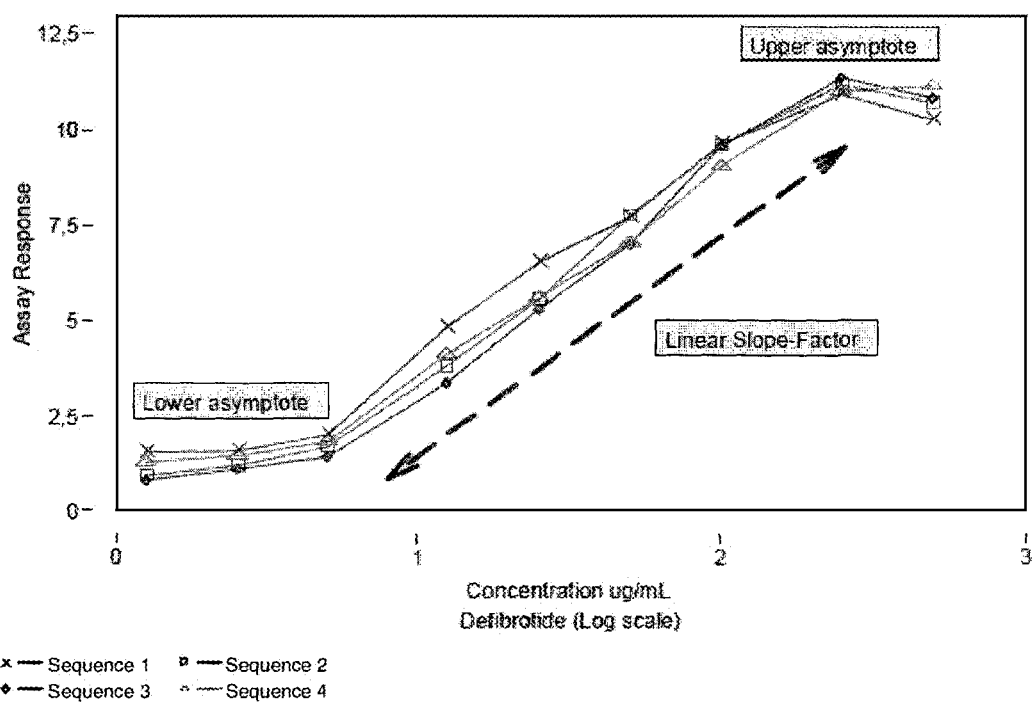
FIG. 2 is a plot illustrating the sigmoid that arises in relation to a standard and test sample of defibrotide.

Graphically, that correlation gives rise to a sigmoid for the standard and a sigmoid for the test sample (FIG. 2); the central portions of the sigmoid have two straight lines which are generally parallel and the distance between which is a function of the difference in biological activity between the test sample and the standard. This interval is used for potency determination using the parallel line model as described by Finney D J, Statistical Method in Biological Assay, 2nd ed. Ch. Griffin, London.

For a more specific determination, the four-parameter logistic curve models is used and in this case the entire sigmoid curve of both, sample and standard, is used for the calculation of the relative biological potency of the sample.

In a preferred embodiment of the present invention, the standard solutions and the solutions of the samples of defibrotide to be determined are introduced into the respective wells of the microplate. The euglobulin fraction are prepared at the moment of use and it is the dilution media of defibrotide stock solution. Finally, the solution containing the chromogenic substrate is added. The microplate is then placed in the thermostated reader and, after rapid agitation, readings of the system's absorbance are taken at predetermined intervals and for the predetermined period of time. The raw data obtained are then processed, thus determining the unknown activities of the defibrotide samples.

As it shall be appreciated from the following examples, the method according to the present invention allows to obtain liquid defibrotide formulations, preferably water solutions, having a defined biological activity and, in particular, having an activity of 25 to 35 IU/mg of defibrotide, preferably from 27.5 to 32.5 IU/mg and, more preferably, from 28 to 32 IU/mg.

Liquid defibrotide formulations are preferably marketed in form of containers, more preferably vials, containing 200 mg of defibrotide in 2.5 ml of buffered water solution (preferably at a pH from 6.5 to 8.5, more preferably from 7 to 8), to be diluted before use; consequently, when the biological activity is assessed with the method of the present invention, each container presents a defibrotide activity of 5000 to 7000 IU, preferably 5500 to 6500 IU, more preferably 5600 to 6400.

Those and other aspects of the invention will be better illustrated in the following examples which are not, however, to be regarded as limiting the invention.

EXAMPLES

The following materials were used in the examples given here:

Apparatus

| Main features: | Microplate reader for UV-Vis absorbance determination equipped with thermostatic chamber and absorbance filter at 405 nm. |
|---|---|
| Detection | Kinetic Absorbance determination at 405 nm |
| Plate Type | 96 · well clear for UV-Vis Determination |
| Chamber Temperature | 37° C. Total Absorbance recording time 45-60 min |
| Absorbance recording frequency | About 1 × min |

Programs & Software
Microsoft Excel® (Microsoft Corporation, Redmond, Wash., USA)
Substances
Defibrotide (Gentium)
Chromogenic substrate S-2251 (Chromogenix Instrumentation Laboratory S.p.A., Milan, Italy)
Tris(hydroxymethyl)aminomethane (TRIS)-NaCl, (Sigma-Aldrich, Milan, Italy)
1N HCl (Carlo Erba reagenti, Milan, Italy)
IN NaOH (Carlo Erba reagenti, Milan, Italy)
Bovine Plasma (Tebu Bio Italia, Magenta (MI), Italy)
Glacial Acetic Acid (Carlo Erba reagenti, Milan, Italy)
Solutions
TRIS-NaCl (1 L Preparation): Into a 1 L beaker quantitatively transfer 6.06 g of TRIS-HCl and 2.2 g of NaCl. Dissolve in 500 mL of purified water and adjust the pH to 7.4 with about 40 mL of HCl 1N. Quantitatively transfer the solution into a volumetric flask of 1 L and dilute the solution to volume with purified water. Store the solution into refrigerator (2-8° C.)
Chromogenic Substrate S2251 (CAS 63589-93-5) 3 mM (15.2 mL Preparation): Dissolve about 25 mg of chromogenic substrate with 15.2 mL of purified water. Store the solution into refrigerator (2-8° C.)
Bovine euglobulins (10 mL Preparation). In a container with a minimum capacity of 300 mL introduce 240 mL of ice-cooled purified water and under stirring add 10 mL bovine plasma. Adjust the pH to 5.3±0.1 with acetic acid 1%. Allow to settle at 2-8° C. for 1 to 16 hours. Remove the clear supernatant solution by siphoning and collect the precipitate by centrifugation at 2.800 rpm for 5 minutes and 4° C. Suspend the precipitate dispersing mechanically (e.g., by means of a laboratory glass rod) in 5 mL of ice-cooled purified water, shake for about 5 min and collect the precipitate by centrifugation at 2.800 rpm for 5 minutes and 4° C. Disperse the precipitate mechanically into about 10 mL of TRIS-NaCl; to facilitate the dissolution of the precipitate crush the particles of the precipitate with a suitable instrument (es.: laboratory glass rod). Store the obtained suspension at 2-8° C. for not less than 1 hour and not more than 6 hours before its use.
Standard and Sample Defibrotide Solutions
Reference Stock Solution
Into 20 mL volumetric flask quantitatively transfer about 100 mg of defibrotide reference standard accurately weighed. Dissolve the powder with about 10 mL TRIS-NaCl and bring the volume with the same solvent. Dilute 1:4 the obtained solution with TRIS-NaCl in order to obtain a defibrotide RS solution of about 1.25 mg/mL.
Sample Stock Solution
Into 20 mL volumetric flask quantitatively transfer about 100 mg of defibrotide sample accurately weighed. Dissolve the powder with about 10 mL TRIS-NaCl and bring the volume with the same solvent. Dilute 1:4 the obtained solution with TRIS-NaCl in order to obtain a defibrotide sample solution of about 1.25 mg/mL.
Reference and Sample Solutions Preparation
a) Defibrotide 125 ug/mL: dilute 1:10 defibrotide stock solution (Reference and Sample) with TRIS NaCl (corresponding to 50 ug/mL into the plate well). Into an eppendorf tube quantitatively transfer 500 uL of the prepared solution and mix with 500 uL of euglobulin. Close the tube and store in ice-cooled water.

b) Defibrotide 62.5 ug/mL: dilute 1:2 solution (a) with TRIS NaCl (corresponding to 25 ug/mL into the plate well), Into an eppendorf tube quantitatively transfer 500 uL of the prepared solution and mix with 500 uL of euglobulin. Close the tube and store in ice-cooled water.

c) Defibrotide 31.25 ug/mL: dilute 1:2 solution (b) with TRIS NaCl (corresponding to 12.5 ug/mL into the plate well). Into an eppendorf tube quantitatively transfer 500 uL of the prepared solution and mix with 500 uL of euglobulin. Close the tube and store in ice-cooled water.

d) Defibrotide 12.5 ug/mL: dilute 1:2.5 solution (d) with TRIS NaCl (corresponding to 5 ug/mL into the plate well). Into an eppendorf tube quantitatively transfer 500 uL of the prepared solution and mix with 500 uL of euglobulin. Close the tube and store in ice-cooled water.

Blank Solution

Mix 1 volume of euglobulins with 1 volume of TRIS NaCl solution (ex.: 500 uL+500 uL)

Plate Deposition

According to the proposed deposition scheme (see Table 1 below) add in each well of the plate 200 uL of standard or sample or blank solution. Note different deposition scheme can be used according to the availability and configuration of automatic pipettes. However not less than 4 depositions for each reference and sample solution must be used for the assay.

Immediately before incubation of the plate into the microplate reader add in each well 50 uL of Chromogenic substrate.

Identification of the linear kinetic range (A@405 nm vs time).

Calculate for each preparation of the standard and of the sample the response of the assay (Slope) in the pre-defined time range as follow.

$$\text{Sample \& Standard Response} = \frac{A_b - A_a}{T_b - T_a} \times 1000$$

Where:
Aa is the Absorbance values at Time Ta (30 min from the plot above)
Ab is the Absorbance value at Time Tb (35 min from the plot above)
Report the obtained value in a tabular format as reported in table 2.

TABLE 2

| Concentration Level | Standard Preparation | | | | Sample Preparation | | | |
|---|---|---|---|---|---|---|---|---|
| [ug/mL] | S1 | S2 | S3 | S4 | U1 | U2 | U3 | U4 |
| 5 | S1_Cd | S2_Cd | S3_Cd | S4_Cd | U1_Cd | U2_Cd | U3_Cd | U4_Cd |
| 12.5 | S1_Cc | S2_Cc | S3_Cc | S4_Cc | U1_Cc | U2_Cc | U3_Cc | U4_Cc |
| 25 | S1_Cb | S2_Cb | S3_Cb | S4_Cb | U1_Cb | U2_Cb | U3_Cb | U4_Cb |
| 50 | S1_Ca | S2_Ca | S3_Ca | S4_Ca | U1_Ca | U2_Ca | U3_Ca | U4_Ca |

Plot the responses for the substance to be examined and for the standard against the logarithms of the concentration and calculate the activity of the substance to be examined using the parallel line model as defined by the relevant 5.3.2 chapter of the Ph. Eur Current edition.

Not less than 3 consecutive serial dilutions of the reference and of the sample should be used (e.g., defibrotide concentration 5 μg/mL, 12.5 μg/mL, 25 μg/mL, 50 μg/mL, or 5 μg/mL, 12.5 μg/mL, 25 μg/mL, or 12.5 μg/mL, 25 μg/mL, 50 μg/mL).

Analysis of the Variance

The analysis of the variance is performed according to the section 5.3.2.3 of the Ph. Eur. current edition and Finney D J (1964) Statistical Method in Biological Assay 2nd ed.

TABLE 1

| | 1 | 2 | 3 | 4 | 5 | 6 | 7 | 8 | 9 | 10 | 11 | 12 |
|---|---|---|---|---|---|---|---|---|---|---|---|---|
| A | — | BLK | S1_Ca | S1_Cb | S1_Cc | S1_Cd | — | — | — | — | — | — |
| B | — | BLK | S2_Ca | S2_Cb | S2_Cc | S2_Cd | — | — | — | — | — | — |
| C | — | BLK | S3_Ca | S3_Cb | S3_Cc | S3_Cd | — | — | — | — | — | — |
| D | — | BLK | S4_Ca | S4_Cb | S4_Cc | S4_Cd | — | — | — | — | — | — |
| E | — | BLK | U1_Ca | U1_Cb | U1_Cc | U1_Cd | — | — | — | — | — | — |
| F | — | BLK | U2_Ca | U2_Cb | U2_Cc | U2_Cd | — | — | — | — | — | — |
| G | — | BLK | U3_Ca | U3_Cb | U3_Cc | U3_Cd | — | — | — | — | — | — |
| H | — | BLK | U4_Ca | U4_Cb | U4_Cc | U4_Cd | — | — | — | — | — | — |

Figure 3:
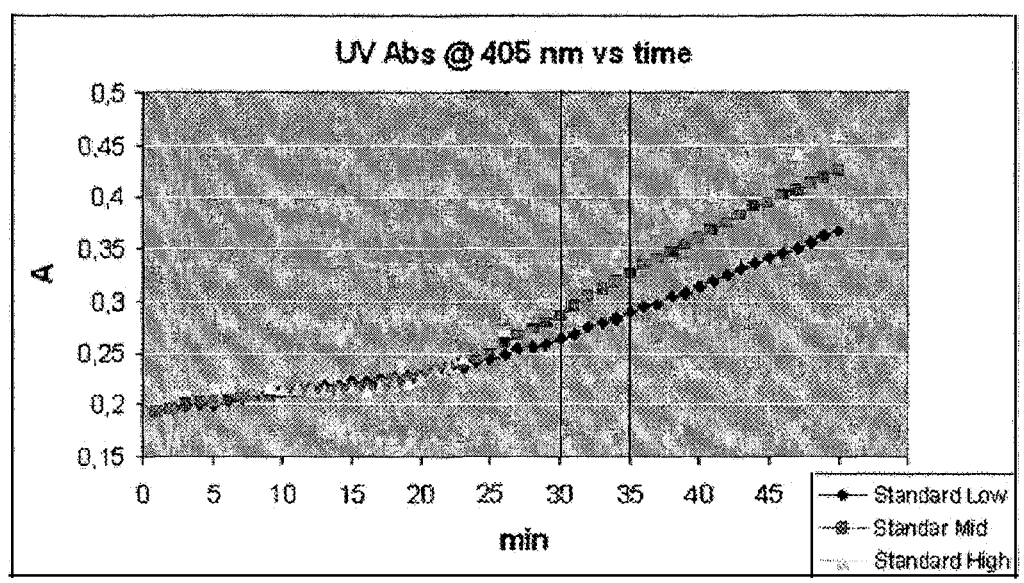
FIG. 3 is a plot showing the "absorbance versus time" of the standard preparations (ex.: S1_Ca, S1_Cb, S1_Cc) identify a suitable linear range (ex.: from 30 to 35 min).

S1, S2, S3, S4: Reference Solution deposition 1, deposition 2, deposition 3, deposition 4,
U1, U2, U2, U5: Sample solution deposition 1, deposition 2 deposition 3, deposition 4,
Ca, Cb, Cc etc.: Defibrotide reference and sample concentration a, b, c etc.
BLK Blank solution Calculation and Results From the kinetic plot "absorbance versus time" of the standard preparations (ex.: S1_Ca, S1_Cb, S1_Cc) identify a suitable linear range (ex.: from 30 to 35 min, see FIG. 3).

Test for Validity
1) The linear regression terms is significant, i.e. the calculated probability is less than 0.05. If this criterion is not met, it is not possible to calculate 95% C.I.
2) The Term of non-parallelism is not significant, i.e. the calculated probability is less than 0.05.

3) The term for non linearity is not significant, i.e. the calculated probability is less than 0.05.

Acceptance Criteria

4) The estimated potency is not less than 90% and not more than 111% of the stated potency.
5) The confidence limits (P=0.95) of the estimated potency are not less than 80% and not more than 125% of the stated potency Calculation Sample Potency (UI/mg) =

$$\frac{R \times \text{Std Potency } (UI/\text{mg}) \times \text{Conc.Std (mg/mL)}}{\text{Conc.Sample (mg/mL)}}$$

where:
R: Result of sample obtained by the parallel line model analysis
Std Potency: Stated potency of the Standard (UI/mg on dry substance)
Conc. Std: Concentration of the Standard (mg/mL on dry substance)
Conc. Sample: Concentration of the Sample (mg/mL on dry substance)

Assay Applied to Defibrotide Formulations

The above-disclosed assay has been used to determine the biological activity of liquid formulations containing 200 mg of defibrotide in 2.5 ml (80 mg per ml) and having the quali-quantitative composition reported in table 3.

TABLE 3

| Component | Reference to Standard Quality | Function | 200 mg Injection | Concentration per mL |
|---|---|---|---|---|
| Defibrotide | In-house standard | Drug Substance | 200.00 mg | 80.00 mg |
| Sodium Citrate, Dihydrate | USP-EP | Buffer | 25.00 mg | 10.00 mg |
| Water-for-injection | USP-EP | Solvent vehicle | q.s. to 2.5 mL | 1.00 mL |
| Sodium hydroxide 1M or hydrochloric acid 1M | NF-EP | pH adjustment | q.s. to 6.8-7.8 | — |
| Nitrogen | NF-EP | Inert gas to displace the air | q.s. | — |

The results are reported in table 4.

TABLE 4

| Batch | Potency IU/mg | Potency IU/container of 200 mg |
|---|---|---|
| 688 | 31 | 6200 |
| 738 | 34 | 6800 |
| 785 | 32 | 6400 |
| 836 | 30 | 6000 |
| 0406 | 31 | 6200 |
| DS0617 | 35 | 7000 |
| DV0502* | * | Not available |
| DV0601 | 35 | 7000 |
| 1070010073 | 32 | 6400 |
| 1080010016 | 32 | 6400 |
| 1080020018 | 31 | 6200 |
| 1080030021 | 31 | 6200 |
| 1080040110 | 32 | 6400 |
| 1080050114 | 35 | 7000 |
| 1080060117 | 34 | 6800 |
| Mean | 33 | |
| Min | 30 | |
| Max | 35 | |
| RSD (%) | 5.4 | |

*Used as Reference Standard

The invention claimed is:

1. A method of treating Veno-Occlusive Disease (VOD) comprising administering to a patient in need thereof a defibrotide formulation consisting of defibrotide, sodium citrate, and water for injection, having a potency of 25 to 35 IU/mg, and a concentration of at least 80 mg/mL, wherein the defibrotide potency is determined by a method comprising the steps of:
   a) bringing into contact defibrotide, mammalian euglobulin and a substrate specific for plasmin which, by reaction with plasmin, provides a measurable product; and
   b) measuring the amount of product formed at successive times, to thereby determine the potency of the defibrotide.

2. The method of claim 1, wherein the formulation has a potency of 27.5 to 32.5 IU/mg.

3. The method of claim 2, wherein the formulation has a potency of 28 to 32 IU/mg.

4. The method of claim 1, wherein the formulation is a water solution.

5. The method of claim 4, wherein the formulation has a pH of from 6.5 to 8.5.

6. The method of claim 5, wherein the formulation has a pH of from 7 to 8.

7. The method of claim 1, wherein the euglobulin is human, rabbit or bovine euglobulin.

8. The method of claim 1, wherein plasmin which reacts with the substrate specific for plasmin is released by plasminogen contained in the mammalian euglobulin.

9. The method of claim 1, wherein the substrate specific for the plasmin is a chromogenic substrate.

10. The method of claim 1, wherein the substrate specific for the plasmin is a compound of formula A1-A2-A3-X in which A1 and A2 are non-polar amino acids, A3 is lysine or arginine and X is the measurable product.

11. The method of claim 10, wherein the measurable product X is selected from the group consisting of para-nitroaniline and 2-naphthylamine.

12. The method of claim 10, wherein the substrate specific for plasmin is H-D-Valyl-L-Leucyl-L-Lysine-p-nitroaniline.

13. The method of claim 10, wherein the measurable product X is measured by spectrophotometry or spectrofluorimetry.

14. The method of claim 1, wherein the mammalian euglobulin is obtained from a volume of plasma and reconstituted to the same volume of the originating plasma or diluted up to 1:10 with suitable buffer and the substrate specific for the plasmin is a chromogenic/fluorogenic substrate having a concentration of from 2.5 to 3.5 mM.

15. The method of claim 1, wherein said method of determining the defibrotide potency is carried out in a reaction medium which is an aqueous solution buffered to a pH of from 7 to 8.

16. The method of claim 1, wherein the method of determining the defibrotide potency is maintained at a temperature of from 35 to 39° C.

17. The method of claim 1, wherein the substrate specific for plasmin has a concentration of from 0.3 to 4 mM.

18. The method of claim 1, wherein the method of determining the defibrotide potency comprises the steps of: c) determining the rate of release of the measurable product during the course of the reaction of both a standard sample and a test sample of defibrotide; d) correlating the rate of release with the corresponding defibrotide concentration to obtain the potency of the test sample of defibrotide.

19. The method of claim 17, wherein the concentration of the substrate specific for plasmin is 3 mM.

* * * * *